US006923064B2

(12) United States Patent
Rodriguez Gobernado et al.

(10) Patent No.: US 6,923,064 B2
(45) Date of Patent: Aug. 2, 2005

(54) METHOD AND DEVICE FOR DETECTION, IDENTIFICATION AND DENSIMETRIC QUANTIFICATION OF GRAIN-EATING INSECTS IN STOCKS OF CEREALS

(75) Inventors: Pedro Rodriguez Gobernado, Valladolid (ES); Francis Fleurat-Lessard, Gradignan (FR); Jose Villamayor, Huesca (ES); Bernard Sautereau, Paris (FR); Giuseppe Brioni, Borgosatollo (IT); Jean Gondolo, Carqueiranne (FR); Bernard Tomasini, Hyeres (FR)

(73) Assignee: Solween Technologies (Societe a Responsabilite Limited), Carquelranne (FR)

( * ) Notice: Subject to any disclaimer, the term of this patent is extended or adjusted under 35 U.S.C. 154(b) by 0 days.

(21) Appl. No.: 10/479,739

(22) PCT Filed: Jun. 7, 2002

(86) PCT No.: PCT/FR02/01958

§ 371 (c)(1),
(2), (4) Date: Apr. 30, 2004

(87) PCT Pub. No.: WO02/101378

PCT Pub. Date: Dec. 19, 2002

(65) Prior Publication Data

US 2004/0193376 A1 Sep. 30, 2004

(30) Foreign Application Priority Data

Jun. 8, 2001  (FR) .............................................. 01 07511

(51) Int. Cl.[7] ............................................. G01N 29/00
(52) U.S. Cl. .............................. 73/587; 73/649; 73/659
(58) Field of Search .......................... 73/587, 649, 659, 73/598, 600, 602

(56) References Cited

U.S. PATENT DOCUMENTS

| | | | | |
|---|---|---|---|---|
| 2,861,132 A | * | 11/1958 | Kahn et al. ................. | 369/174 |
| 3,886,492 A | * | 5/1975 | White ........................ | 367/139 |
| 4,445,788 A | | 5/1984 | Twersky et al. | |
| 4,809,554 A | | 3/1989 | Shade et al. | |
| 4,895,025 A | * | 1/1990 | Betts .......................... | 73/587 |
| 4,937,555 A | | 6/1990 | Litzkow et al. | |
| 5,005,416 A | | 4/1991 | Vick et al. | |
| 5,285,688 A | * | 2/1994 | Robbins et al. ............... | 73/587 |
| 5,473,942 A | * | 12/1995 | Vick et al. ..................... | 73/587 |
| 6,493,363 B1 | * | 12/2002 | Shuman et al. ............. | 370/539 |

* cited by examiner

Primary Examiner—Hezron Williams
Assistant Examiner—Jacques M. Saint-Surin
(74) Attorney, Agent, or Firm—Egbert Law Offices

(57) ABSTRACT

A method and a device for detection, classification and densimetric quantification of grain-eating insects, of one or several families of insects simultaneously present, in stocks of cereals and the like, which includes detecting insects through noises and sound and/or infrasonic vibrations emitted by the insects. It also includes carrying out the following operations: recording the real noises in the stock, eliminating known spurious noises, detecting on the resulting envelope energy curve windows corresponding to energy peaks and determining therefrom the mean frequency, the spectral width and the global energy, comparing the mean frequency and the width of each of the windows to that of windows with similar known and listed characteristics, so as to operate a taxonomic classification, finally, comparing the mean frequency and the global energy of each of the windows, to those of windows with known and listed characteristics, to operate a densimetric quanitification.

10 Claims, 1 Drawing Sheet

METHOD AND DEVICE FOR DETECTION, IDENTIFICATION AND DENSIMETRIC QUANTIFICATION OF GRAIN-EATING INSECTS IN STOCKS OF CEREALS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to a method, and a device for its implementation, for detecting, classifying and densimetrically quantifying insects, of one or several families simultaneously present, in stocks of foodstuffs likely to be infested, such as stocks of cereals.

BACKGROUND OF THE INVENTION

In the field of agriculture and foodstuff, insects cause important damage both at the level of the crops and at the level of the storage of the products.

Generally, a systematic insecticidal treatment is carried out to eliminate the insects.

Though it is relatively easy to determine the nature and the density of insects by means of a mere visual checking of the portion of the crops above the ground, the same does not apply to the products, in particular cereals, when they are stored or transported whether in a warehouse, a silo or a truck, since it is very difficult to detect the degree of infestation inside the batch.

Presently, the analysis is carried out by sieving one or several samples. However, the infestation can be uniform or not, and be developed more or less in depth. Therefore, in order to obtain less random results, samples are taken in the areas which insects are likely to shelter, for example in the areas where a rise in temperature has been observed, which can be a sign for the presence of insects.

If only one insect is discovered in a sample, the treatment of the whole batch is carried out, and if no an insect is discovered in the samples, it frequently occurs that, in case of doubt, one also treats the whole batch. Thus, systematic applications of insecticides are observed, which result into an over-treatment.

The drawback of this process is that the treatments used are carried out based on chemicals, which are often toxic ones.

One distinguishes two types of treatment, the shock treatment and the remanent treatment. The shock treatment is based on the use of dichlorvos, which is classified as toxic, which kills all the insects within 2 or 3 hours, and which, because of its high volatility, almost completely disappears within 48 hours. The remanent treatment uses slowly degrading molecules which allow a remanent action of the insecticide, their effectiveness is spread over a longer time, it takes 72 hours to kill all the insects, and the destruction of new insects is ensured for at least 3 to 4 months.

The use of insecticides is presently a very strong concern with cereal growers, in particular with the processors, who will thus proscribe insecticides in the short run, while asking for insect-free cereals.

There are alternative methods allowing fighting against the infestation by insects, primarily based on a cooling of the stocks by ventilation. These methods can allow limiting the over-treatments, but require, on the other hand, a rigorous follow-up of the stocks and reliable insect-detecting methods.

There have already been provided devices allowing detecting the presence of insects, and eventually their classification as well as their quantification. Most of these devices are seldom used, because they implement detecting means, collecting means and analyzing means the use of which is complex.

Thus, from U.S. Pat. No. 5,646,404 are known an apparatus and a method for quantitatively detecting granivorous insects, said apparatus comprising infrared means capable of detecting the insects contained in a quantity of grains passing though a channel. This device consists, in fact, of an improved sieve, the result of which depends, here too, on the place of sampling.

There are also known detecting methods using means capable of detecting the insects by listening to the noises they make, whether it be displacement, chewing or other noises. These methods are however confronted with some problems, in particular that of random noise likely to distort the result, and, in addition, that of allowing only with difficulty a classification and a densimetric quantification of the insects.

U.S. Pat. No. 4,991,439 discloses an apparatus of this type, using a piezoelectric crystal for detecting the vibrations produced by the granivorous insects, thus allowing, by analyzing the vibrations and by comparing them with known vibrations, determining the species involved. This apparatus is provided according to two embodiments, one that can be used directly in the stocks and the other one by analyzing a sample. The apparatuses are not very reliable from the point of view of the result, because of the random noise. That is why the one operating by means of sampling is preferred, because it allows moving the sample to a quiet place to carry out the analysis of same in the absence of random noise.

The inventor of these apparatuses had already tried to solve the problem arising from the presence of insects in a stock of cereals, and he developed an apparatus for detecting and classifying insects, which is described in U.S. Pat. No. 4,895,025. With this apparatus are recorded the acoustic signals emitted by the insects, said signals are averaged, and the average magnitude according to the frequency is compared with known data corresponding to a type of insects.

This method indeed allows classifying the insects, but, besides the fact that averaging the frequency of signals is not applicable in the case of a practical use in an operational environment, this method has the drawback of not allowing differentiating the insects when the medium being tested contains several families of them. In this case, since it is not possible to accurately classify the various families of insects present in the stocks, it is difficult to contemplate a densimetric quantification.

BRIEF SUMMARY OF THE INVENTION

The purpose of the present invention is to provide a method for detecting, classifying and densimetrically quantifying granivorous insects, of one or several families of insects simultaneously present, in stocks of cereals or the like, which allows coping with the various above-mentioned drawbacks, while being easy to be used, relatively simple and inexpensive to be manufactured in comparison with the existing devices.

The present invention is also aimed at providing a device for implementing the method according to the invention, and which is construed so as to carry out three functions:

the detection of the possible presence of insects in the volume of grains being tested, the classification of the species and the stage, larvae or adults, of the detected insects, and the assessment of the density of population of the detected insects, i.e. the importance of the infestation.

It should be noted that the method according to the invention is not limited to a use in cereal products, it is thus possible to use it in other products, such as oilseeds, for example.

The method for detecting, classifying and densimetrically quantifying granivorous insects, of one or several families of insects simultaneously present, in stocks of cereals or the like according to the invention is of the type consisting in detecting said insects through the noises and sound and/or infrasonic vibrations they emit, and it is essentially characterized in that it consists in carrying out the following operations:

recording the actual noises in said stocks, eliminating the known random noise, detecting on the envelope energy curve obtained from possible windows corresponding to energy peaks and determining the average frequency, the spectral width and total energy, comparing the average frequency and the width of each of said windows with those of known and indexed windows of similar characteristics, in order to carry out a taxinomic classification, and finally, comparing the average frequency and the total energy of each of said windows with those of known and indexed windows of similar characteristics, in order to carry out a densimetric quantification.

The method according to the invention allows detecting the presence of insects, but also classifying the latter and quantifying them, while directly recording, without sampling, the actual noises and vibrations in the stocks.

According to an additional feature of the method according to the invention, the following operations are also carried out:

analyzing the curve of frequencies and detecting windows of frequency corresponding to frequency peaks, and determining their average frequency and their spectral width, comparing the curves of energy and frequency, and eliminating the windows corresponding to non-matching peaks of energy or frequency, and comparing the windows corresponding to peaks of frequency of the remaining pairs with known and indexed similar values, in order to determine the taxonomy and the stage of development.

This additional feature allows making the obtained result reliable, it allows in addition a sharper classification of the species and in particular of the stage of development, larva or adult, for example.

According to another additional feature of the method according to the invention, temperature and/or hygroscopy measurements are carried out, which are integrated into the signal processing, so as to balance the obtained result.

Taking into account the temperature and/or the percentage of moisture of the grain allows refining the result as regards the taxinomic classification, since the conditions most favorable to an infestation by a given species are known, and can therefore be classified in the same way as the average frequency, spectral width and total energy values of the windows corresponding to the energy peaks, and the average frequency and spectral width values of the windows corresponding to the frequency peaks.

The device allowing implementing the method according to the invention is of the type comprising means allowing detecting the sound and/or infrasonic noises emitted by insects in stocks of cereals, and is essentially characterized in that it comprises, on the one hand, at least a rectilinear supporting means capable of being inserted into the stock of cereals, or the like, to a determined depth, said supporting means carrying one or more of said sensor means; on the other hand, means for processing the detected signals; and, still on the other hand, means for displaying the results.

According to an additional feature of the device according to the invention, it includes several sensor means distributed alongside the supporting means.

According to a particular embodiment of the device according to the invention, the supporting means consists of a tubular member the free end of which is in the form of a tip.

According to another additional feature of the device according to the invention, the supporting means is provided with gripping means authorizing its handling and its transportation by an operator.

According to another additional feature of the device according to the invention, it includes several supporting means each equipped with one or several sensor means, and with means for processing the detected signals, said processing means being connected to a control unit capable of analyzing the results recorded by said processing means and of displaying said results.

According to this variant, it is possible to use several supporting means inserted at various locations of the cereal heap, so as to simultaneously carry out several measurements likely to accelerate the rhythms, the various locations of insertion of said supporting means with respect to the configuration of the heap being likely to be predetermined and even integrated into the signal-processing operation.

The various supporting means can be placed separately by an operator, they can also be physically connected, and be actuated by a handling robot capable of carrying out, automatically or on request, measurements both in a silo or in the trailer of a freight vehicle.

According to another additional feature of the device according to the invention, the means for processing the detected signals includes means capable of ensuring the acquisition of data coming from the sensors, means capable of carrying out the processing of the data acquired or being acquired, means for controlling the interface with the user, a dynamically re-configurable insect-profile data bank, means for storing the results of the treatments carried out during a series of measurements, transmission means capable of ensuring the transmission of data to an external calculator through any data-processing communication means.

The advantages and the features of the device according to the invention will become clear from the following description with reference to the attached drawing, which represents a non-restrictive embodiment of it.

BRIEF DESCRIPTION OF THE SEVERAL VIEWS OF THE DRAWINGS

In the attached drawings, the following figures are shown.

DETAILED DESCRIPTION OF THE INVENTION

Figure 1:
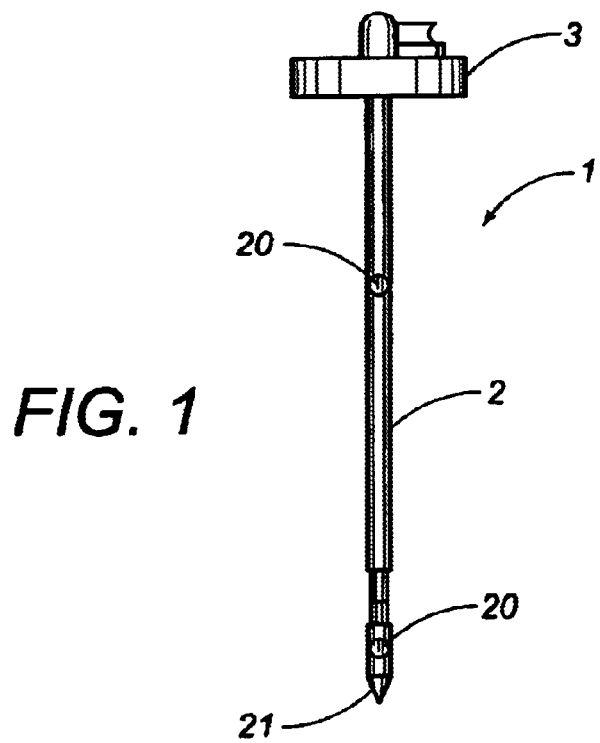
FIG. 1 is a schematic elevation view of a device according to the invention.

When referring to FIG. 1, one can see that a device 1 for detecting, classifying and densimetrically quantifying insects or families of insects in stocks of foodstuffs likely to be infested, namely stocks of cereals, according to the invention essentially comprises two parts, namely a cane 2 aimed at being inserted into the stock of products to be checked, and a head 3.

The cane 2 includes several detecting modules 20 distributed longitudinally, in this case two, one at a short distance from the free end, and the other one in the central area.

The cane 2 also includes a conical end 21 facilitating the insertion into the material, and containing an ambient temperature gauge with low thermal inertia, and eventually a moisture sensor.

It should be noted that the cane 2 can include mechanical means, eventually motorized means, for facilitating the penetration into the material. These means can be, for example, helically shaped members such as drills.

The head 3 contains an electronic system allowing ensuring the acquisition of the data coming from the detecting modules 20, it performs the processing of the data acquired or being acquired.

The electronic system controls the interface with the user in the operational mode of the apparatus, it integrates a dynamically re-configurable insect-profile memory, it is capable of storing the results of the treatments carried out during a series of measurements.

It can also ensure the transmission of data to an external calculator, through any data-processing communication means.

In this embodiment, it incorporates an autonomous and rechargeable electric power supply unit, facilitating its displacement and thus its use, to carry out successive recordings at various locations.

Figure 2:
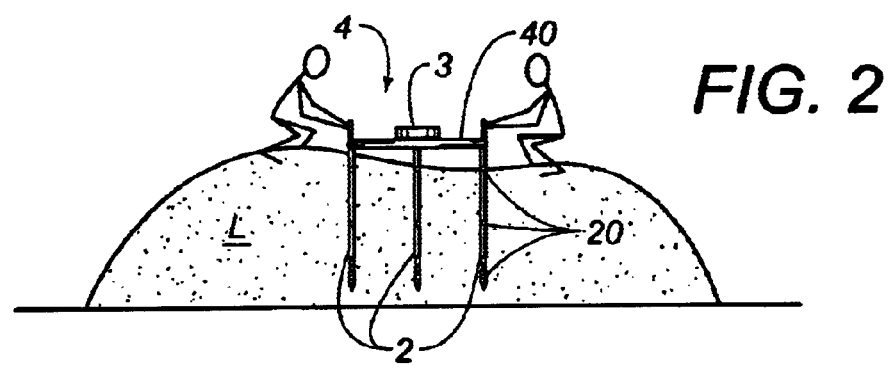
FIG. 2 is a schematic view of a variant of the same device, during its use.

Referring now to FIG. 2, one can see a variant 4 of the device according to the invention, which comprises several canes 2 connected by means of a frame 40 maintaining them at a determined distance from each other, and which carries a head 3.

This variant 4 allows carrying out multiple measurements at the same time, this in order to reduce the total time of analysis of a batch or to make a three-dimensional measurement in volume.

The data can advantageously be transmitted to a unit which controls them and can store them and print them, the transmission occurring preferably by radio link or the like.

In FIG. 2, the device according to the invention is handled by two operators, who move it and insert the canes 2 into a batch L of cereals, it is however obviously possible to mechanize the displacement of the device, by means of a robot, for example.

Figure 3:
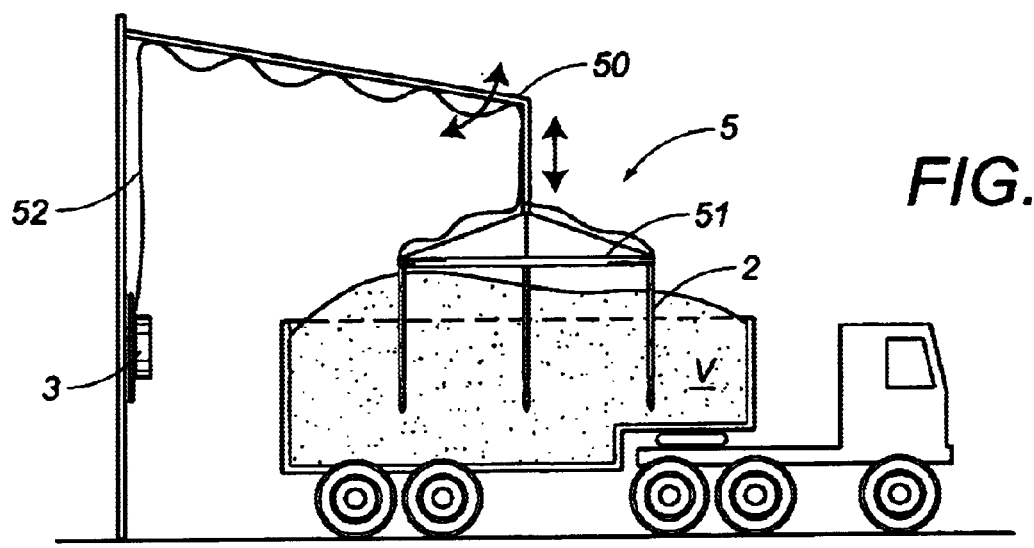
FIG. 3 is a schematic view of another variant of the same device, during its use.

Thus, when referring to FIG. 3, one can see a device 5 according to the invention, in a variant, comprising a mechanical arm 50 for carrying out an automatic checking in a batch of cereals, here in a batch L contained in the trailer of a freight vehicle V.

The device 5 comprises canes 2 connected by means of a frame 51, which is suspended from the mechanical arm 50 which allows moving the canes 2. In this embodiment, the data collected by the canes 2 are transmitted by means of cable connections 52 to a head 3 arranged upstream of the mechanical arm 50.

It should be noted that a similar installation assembled to residence in a silo can be used as a permanent monitoring system.

We claim:

1. Method for detecting, classifying and densimetrically quantifying granivorous insects, of one or several families of insects simultaneously present, in stocks of cereals said method detecting said insects through noises and sound and/or infrasonic vibrations which the insects emit, said method comprising:

recording actual noises in said stocks, eliminating known random noise, detecting on an envelope energy curve obtained from possible windows corresponding to energy peaks and determining average frequency, spectral width and total energy, comparing average frequency and width of each of said windows with those of known and indexed windows of similar characteristics, in order to carry out a taxinomic classification, and comparing the average frequency and the total energy of each of said windows with those of known and indexed windows of similar characteristics, in order to carry out a densimetric quantification.

2. Method according to claim 1, further comprising:

analyzing a curve of frequencies and detecting windows of frequency corresponding to frequency peaks, and determining their average frequency and their spectral width, comparing the curves of energy and frequency, and eliminating the windows corresponding to non-matching peaks of energy or frequency, and comparing the windows corresponding to peaks of frequency of the remaining pairs with known and indexed similar values, in order to determine the taxonomy and the stage of development.

3. Method according to claim 1, further comprising: carrying out temperature and/or hygroscopy measurements, which are integrated into the signal processing, so as to balance the obtained result.

4. Device allowing implementing the method according to claim 1, comprising:

means allowing detecting the sound and/or infrasonic noises emitted by insects in stocks of cereals or the like, being comprised of, at least rectilinear supporting means capable of being inserted into the stock of cereals, to a determined depth, said supporting means carrying one or more of said sensor means; and a means for processing the detected signals; and, means for displaying results.

5. Device according to claim 4, further comprising: several sensor means distributed alongside the supporting means.

6. Device according to claim 4, wherein said supporting means is comprised of a tabular member the free end of which is in the form of a tip.

7. Device according to claim 4, wherein said supporting means is comprised of gripping means authorizing its handling and its transportation by an operator.

8. Device according to claim 4, further comprising: several supporting means each equipped with one or several sensor means, and means for processing the detected signals, said processing means being connected to a control unit capable of analyzing the results recorded by said processing means and of displaying said results.

9. Device according to claim 4, wherein said supporting means are physically connected, and are capable of being actuated by a handling robot.

10. Device according to claim 4, wherein said means for processing the detected signals comprises means capable of ensuring the acquisition of data coming from the sensors, means capable of carrying out the processing of the data acquired or being acquired, means for controlling the interface with the user, a dynamically re-configurable insect-profile data bank, means for storing the results of the treatments carried out during a series of measurements, transmission means capable of ensuring the transmission of data to an external calculator through any data-processing communication means.

\* \* \* \* \*